US008709231B2

(12) United States Patent
Lascoste et al.

(10) Patent No.: US 8,709,231 B2
(45) Date of Patent: Apr. 29, 2014

(54) METHOD FOR ENRICHING WATER WITH OXYGEN BY AN ELECTROLYTIC PROCESS, OXYGEN ENRICHED WATER OR BEVERAGE AND USES THEREOF

(75) Inventors: Christophe Lascoste, Limours (FR); Stéphane Brunner, Athis Mons (FR); Liliana Jimenez, Gif S/Yvette (FR); Alexis Klein, Paris (FR)

(73) Assignee: Compagnie Gervais Danone, Paris (FR)

( * ) Notice: Subject to any disclaimer, the term of this patent is extended or adjusted under 35 U.S.C. 154(b) by 422 days.

(21) Appl. No.: 12/809,461

(22) PCT Filed: Dec. 19, 2008

(86) PCT No.: PCT/EP2008/067982
§ 371 (c)(1),
(2), (4) Date: Nov. 18, 2010

(87) PCT Pub. No.: WO2009/083489
PCT Pub. Date: Jul. 9, 2009

(65) Prior Publication Data
US 2011/0064824 A1 Mar. 17, 2011

(30) Foreign Application Priority Data

Dec. 21, 2007 (FR) ..................................... 07 60310

(51) Int. Cl.
*C02F 1/46* (2006.01)
(52) U.S. Cl.
USPC ............ 205/701; 205/742; 205/746; 205/756
(58) Field of Classification Search
USPC .................................. 205/701, 742, 746, 756
See application file for complete search history.

(56) References Cited

U.S. PATENT DOCUMENTS

| 5,615,764 | A | 4/1997 | Satoh |
| 5,616,221 | A * | 4/1997 | Aoki et al. ..................... 204/252 |
| 5,728,287 | A * | 3/1998 | Hough et al. .................. 205/743 |
| 6,572,902 | B2 * | 6/2003 | Abramowitz et al. .......... 426/66 |
| 6,652,719 | B1 | 11/2003 | Tseng |
| 2006/0169575 | A1 | 8/2006 | Sumita |
| 2006/0273043 | A1 | 12/2006 | Bagley |
| 2006/0292266 | A1 | 12/2006 | Okuda |

FOREIGN PATENT DOCUMENTS

| DE | 20101692 U1 | 7/2001 |
| EP | 1293481 A2 | 3/2003 |
| EP | 1512670 A1 | 3/2005 |
| EP | 1826183 A1 | 8/2007 |

(Continued)

OTHER PUBLICATIONS

French Search Report dated Aug. 13, 2008, for French Application No. FR 0760310.

(Continued)

*Primary Examiner* — Arun S Phasge
(74) *Attorney, Agent, or Firm* — Finnegen, Henderson, Farabow, Garrett & Dunner LLP

(57) ABSTRACT

The invention relates to a method for enriching water with oxygen by an electrolytic process, that comprises the following series of steps: the electrolysis of $Cl^-$ $Br^-$ ion-free water in an electrolysis cell in which the anode and the cathode are separated by a gas-tight membrane that is pervious to electric charges; b) recovering the oxygen-enriched water from the anode compartment of the electrolysis cell.

9 Claims, 10 Drawing Sheets

(56) References Cited

FOREIGN PATENT DOCUMENTS

| | | |
|---|---|---|
| GB | 2294590 A | 5/1996 |
| JP | 7-303885 | 11/1995 |
| JP | 11-262753 | 9/1999 |
| JP | 2006 043681 A | 2/2006 |
| WO | WO 02/085974 A1 | 10/2002 |
| WO | WO 03/042112 A1 | 5/2003 |
| WO | WO 2006/023876 A1 | 3/2006 |

OTHER PUBLICATIONS

International Search Report dated Jun. 3, 2009, for International Application No. PCT/EP2008/067982.

* cited by examiner

METHOD FOR ENRICHING WATER WITH OXYGEN BY AN ELECTROLYTIC PROCESS, OXYGEN ENRICHED WATER OR BEVERAGE AND USES THEREOF

The invention relates to water or beverages enriched with oxygen ($O_2$), their method of production and their uses.

The world consumption of bottled water is continuously increasing, consumers seeking water of quality from sensorial and quality viewpoints (presence of minerals, no chlorine or polluting elements). The market for water and so-called functional beverages is constantly progressing.

In Japan, the consumption of alkaline water is rapidly expanding. Although scientific evidence still remains limited, the advantage of this water is apparently its taste, its capacity to reduce the too high acidification of some body fluids (gastric fluid, blood), improved cooking properties for some foods (tea, rice, bread). This water is most often obtained by an electrolytic process in which electrolysis cells with two compartments are used (one compartment for the anode, another for the cathode) separated by a membrane. In this method, the water is optionally filtered through activated carbon (to remove particles, residual chlorine) without modifying its mineral composition, and it is then subjected to electrolysis which produces two flows (a base flow and an acid flow) of which only the base flow (alkaline water) is collected. Said electrolysis cells are marketed by NICHIDEN and JAPAN CARLIT for example.

However, the alleged benefits of this alkaline water have not yet been scientifically proven.

It may also be of interest to offer consumers water/functional beverages having a health benefit, in particular intended to increase the physical performances of consumers, tolerance to effort and capacity to recover.

For this purpose the invention proposes oxygen-enriched water. Oxygen is indispensable for the functioning of tissues and organs, which require larger oxygen intake during physical effort. In this oxygen-enriched water, the oxygen is bioavailable and its absorption by the body has been proven by the inventors. This oxygen-enriched water can notably increase oxygen supply to the tissues, improve physical performances, aid physical performances, prolong physical effort, increase tolerance to effort, improve recovery rate and finally prevent dehydration.

Water said to be oxygen-enriched has already been claimed in the prior art. Mention may be made for example of American application US 2006/0 273 043 and all the American applications of the same family filed by Mr. Bagley. This American application claims a method to produce structured, alkaline water that is super-oxygenated and has a negative oxidation-reduction potential. In this method, the water is pre-conditioned through a series of filters (0.5-5-10 μm) then filtered through activated carbon, treated with UV (ultraviolet) and $O_3$ (ozone) before undergoing a magnetic structuring step with magnets. This pre-conditioning does not modify the mineral composition of the water but may generate hazardous by-products (bromates) due to the use of ozone. The water is then subjected to electrolysis with a view to obtaining alkaline water with negative oxidation-reduction potential. In the electrolysis cell used, the anode and cathode compartments are separate. This electrolysis step therefore produces two flows (an alkaline flow and an acidic flow) of which only the alkaline flow is collected (the acidic-anode-flow being a by-product with potential use in cleaning applications). Oxygen is then injected. The injected oxygen is produced by an air compressor which supplies an oxygen generator. The oxygen is then purified (carbon) and activated by magnetization (magnets) before injection. This system is completed by another injection of oxygen of medical quality.

The described method preferably comprises passing of the water in a cone system to perfect the water/oxygen mixture, then in a coil system which also ensures close mixing of the water and oxygen (optionally ozone is also added). Said systems induce residence times which are too long to envisage industrialization. In addition, the use of ozone may generate secondary products. It is also to be pointed out that this method induces significant water losses, the content of the anode compartment being a by-product which is not valued in the same technical area.

The described method therefore leads to water that is enriched with oxygen, the oxygen present in the water being derived from the injection step, having a negative oxidation-reduction potential (in the order of −170 mV, the reference electrode not being indicated however).

Another method to produce water enriched with oxygen is also described in international application WO 2006/023 876. More precisely, this application describes a method and the associated way to prepare enhanced-solubility water (ESW) in relation to oxygen. Its principle is based on the electromagnetic treatment of water using pulses of current. After tests to evaluate this method, it appears to us that it is not valid for the following reasons:

formation of by-products due to the effect of electrolysis; bromate ions $BrO_3^-$, chlorate ions $ClO_3^-$, chlorine $Cl_2$, hypochlorite $ClO^-$, hypochlorous acid $HClO$, ozone $O_3$, trihalomethanes THM. These species are subject to severe regulations on account of their toxic or carcinogenic nature. They are systematically generated by electrolysis of water, if the $Cl^-$ and $Br^-$ species are initially present in the water before electrolysis. Yet, these species are omnipresent in potable waters, surface water or spring water, and very low concentrations of these species in the order of the mg/l for chlorides and μg/l for bromides are sufficient to generate unacceptable levels of by-products. This phenomenon can be reduced depending on the type of electrode used but it still remains. Therefore, the water generated by the method described in this application does not conform to regulations for bottled water. In addition, during these same tests, some of these chlorine by-products generated unpleasant tastes and odours unacceptable for consumers.

Simultaneous generation of $O_2$ and $H_2$. During the electromagnetic treatment, the reactions involved lead to the onset of $O_2$ at the anode and of $H_2$ at the cathode. These two gases are generated in stoichiometric proportions allowing the exothermal and explosive reaction: $H_2+\frac{1}{2}O_2 \rightarrow H_2O$: a reaction used in fuel cells. To overcome this risk, the inventors cause the $H_2$ to be removed via a vent located on tank "116" coupled with filtered flushing of atmospheric air. It appears difficult to guarantee complete evacuation of the hydrogen formed without losing a large part of the $O_2$ formed by electrolysis. Industrialization of this technology could therefore prove to be hazardous since the two gases co-exist within the system.

Partial control over the $O_2$ produced by electrolysis: the pressure and temperature conditions of the water in tank "116" are: 2 relative bars and 1° C. At these values, by extended contact between the water and flushed air to evacuate the $H_2$ present in the tank, the concentration of $O_2$ dissolved in the water at equilibrium will settle at between 35 and 40 mg/l of $O_2$. This equilibrium value is given by Henry's law and is therefore obtained independently of electrolysis functioning! Yet, according to this same patent, this corresponds to the enrichment values obtained after 3 to 4 hours of electrolysis (28-35 mg/l of dissolved $O_2$). Under these conditions, it is certain that not all the oxygen present in the water after treatment is derived from electrolysis, but is the sum of $O_2$ transferred by air flushing in this tank and of the $O_2$ produced by electrolysis.

Stability of $O_2$ dissolved in the water: this stability is said to be greater than that obtained by injection of $O_2$, without any demonstration being given of this difference. Yet, to date, all our comparative tests show that the stability of $O_2$ whether obtained by electrolysis or injection is the same. On the other hand, this experimental stability proves to be greater than theoretical stability, since the decrease in the value of dissolved $O_2$ is observed over a period in the order of 20 days and not a few hours as suggested by theory (cf. Example 2 on stability).

The clinical studies reported do not pay heed to good measurement practice (no monitoring of expired gases; no assay of plasma lactic acid to verify whether the subjects have or have not reached their physical limit). Their scientific validity, their results and their conclusions are therefore questionable.

The described electrodes, anode and cathode, are both in solid titanium coated with platinum. The cost price of said electrodes is too high to contemplate industrialization.

The overall yield of the method is low: in addition to high $O_2$ losses (partly lost at the same time as $H_2$), the method provides for recirculation operations for 3 to 4 hours before generating the end product.

Persons skilled in the art are therefore continuing to search for a method to obtain oxygen-enriched water that is economically viable and can be easily industrialized. In particular, the inventors have sought to develop an electrolysis method which effectively enables water to be enriched with oxygen ($O_2$) whilst overcoming the formation of by-products in particular halogen by-products.

The first subject of the invention is a method to enrich water with oxygen by electrolytic route comprising the following successive steps:

a) electrolysis of mineralized water free of $Cl^-$ and $Br^-$ ions, in an electrolysis cell in which the anode and the cathode are separated by a membrane pervious to electric charges but impervious to gases;

b) collection of the oxygen-enriched water derived from the anode compartment of the electrolysis cell, c) re-injection of the water derived from the cathode compartment of the electrolysis cell, free of hydrogen, into the oxygen-enriched water obtained at step (b), d) packaging the water obtained at step (c).

By "oxygen" is meant the oxygen which can be directly absorbed by the cells designated by the chemical formula $O_2$.

Oxygen enrichment is the addition of oxygen $O_2$ to the water such that the quantity of dissolved oxygen is greater than 10 mg/l, advantageously greater than 50 mg/l, further advantageously greater than 100 mg/l.

By packaging is meant any storage system and/or water dispensing system also allowing the properties of said water to be preserved. Therefore packaging is adapted for human consumption of the water comprised therein.

The expression "$Cl^-$ and $Br^-$ ion-free water" means that the water comprises less than 0.2 mg/l chloride ions and less than 3 µg/l bromide ions.

The cathode is the electrode that is the site of the reduction, whereas the anode is the electrode that is the site of oxidation.

The method of the invention is characterized in that in the electrolysis cell, the two electrodes, the cathode and anode, are separated by a membrane pervious to electric charges (to cations in particular) but not to gases. The use of said membrane allows any co-existence to be avoided between hydrogen $H_2$ and oxygen $O_2$, with its associated risk of explosion.

The transport of ions through the membrane is governed by three principles:
   influence of the electric field imposed by the current generator),
   concentration gradient of each species either side of the membrane,
   osmotic pressure generating the passing of water to dilute the most concentrated side.

The membrane used in the method of the invention makes it possible to confine the oxygen $O_2$ on the anode side and the hydrogen $H_2$ on the cathode side. At the same time, it allows the transport of ions from one compartment to the other, in particular the transport of $H^+$ protons. The membrane used is advantageously a cationic membrane which allows the priority passing of cations. It may allow all the cations to pass, or it may be monovalent-cation selective (only the monovalent cations are able to pass through this membrane). Preferably the membrane used is approved for food use.

Any (organic) membrane allowing this function to be met may be used. As an example, it is possible to mention the membrane sold under the trade name Nafion® manufactured by DuPont de Nemours. This cationic membrane is a sulphonated tetrafluoroethylene copolymer which, when wet, has very good capability to transport protons ($H^+$) whilst having good mechanical and heat resistance. It also has very good resistance to oxidation and to some chemical products (chlorine, sodium hydroxide). Mention may also be made of the membrane sold under the trade name Neosepta® manufactured by Tokuyama, in particular the membranes sold under the trade name Neosepta® in the CMX range such as CMX-Sb and CMX-S. These Neosepta® membranes in the CMX range are cationic, symmetric non-oriented membranes, in a styrene-divinylbenzene copolymer. The Neosepta® membrane in the CMX-Sb range is a dense, standard cationic membrane that is non-selective, food-safe and much cheaper than the Nafion membrane. The Neosepta® membrane in the CMX-S range is a monovalent-cation selective membrane approved for food applications in Europe, food-grade approval pending in the United States.

The solubility of gases in water can be determined according to Henry's law. Under this law, at constant temperature and at saturation, the quantity of gas dissolved in a liquid is proportional to the pressure exerted by this gas on the liquid. For example, in one liter of water 49.1 ml of $O_2$ can be dissolved at 0° C., whereas only 20.9 ml of $O_2$ can be dissolved at 50° C., with an oxygen partial pressure of 1 bar.

For this reason, it is preferable that the water subjected to the electrolysis step should be at a temperature which can ensure the maintaining of the oxygen $O_2$ formed in the water. According to one advantageous variant of the invention, the $Cl^-$ and $Br^-$ ion-free water is cooled to between 1 and 10° C. before being directed under pressure (advantageously $6.10^5$ Pa) into the electrolysis cell. During the electrolysis step, the temperature of the water is advantageously held at between 1 and 10° C.

According to one advantageous variant of the method of the invention, the entering flow of water is divided into 2 branches of identical flow rate which each pass through one of the 2 compartments, anode or cathode. These 2 compartments are separated by an organic membrane pervious to electric charges but impervious to gases, such as described previously. Depending on the type of cell, it may be judicious to conduct recirculation on each of the compartments. This recirculation can permit temperature adjustment by means of a heat exchanger and servo-control of the electric power applied in relation to the desired oxygen content. Electrolysis generates oxygen enrichment of the anode flow and the production of hydrogen in the cathode flow. The formed hydrogen is removed, as and when it is produced, by a hollow fibre membrane module operating under a partial vacuum advantageously with nitrogen flushing. This hollow fibre membrane module uses gas-pervious but water-impervious membranes. The use of this module allows removal of the dissolved hydrogen. At the output of the electrolysis unit, the 2 branches join together to form a mixture with neutral pH, enriched with $O_2$ and free of $H_2$ (self-neutralization). Self-neutralization is the addition of the water derived from the cathode compartment whose dissolved hydrogen has been removed, to the water derived from the anode compartment, advantageously at a ratio of 1:1.

Rapid recirculation on each side of the membrane leads to optimized yield of gas production/electrode surface. According to one advantageous variant of the method, on each branch there is a recirculation loop whose flow rate is 2 to 20 times the nominal flow rate of the installation, which allows for better hydraulics in the electrolysis cell: improved mixing of water and gas (turbulent flow), entraining of the gas boundary layer which may form on the surface of the electrode. The recirculation water is remixed at the entry to the electrolysis cell with water which has not yet undergone an electrolysis step. This circulation remains optional however. It is more advantageous to deliberately choose conditions of pressure and temperature which can avoid the formation of gas pockets. Recirculation then becomes unnecessary.

During this electrolysis step, the pressure is maintained at $6.10^5$ Pa. Ascertained pressure loss is advantageously less than $1.10^5$ Pa.

The total flow rate of water at the input and output of the electrolysis cell advantageously varies between 10 l/h and 50 l/h. The recirculation flow rate may be 120 l/h.

In the method of the invention, it is not necessary for the two electrodes (anode and cathode) to be in solid titanium coated with platinum. According to one advantageous variant of the invention, only the anode is an electrode in solid titanium coated with platinum. The cathode may simply be a stainless steel cathode, which contributes towards reducing the overall cost of the method most significantly (the savings generated are around 20% of the full cost of the installation). Also, an electrode in stainless steel has the advantage of being food-safe (unlike other electrodes).

The water pressures at the input to the anode and cathode are controlled; they must be in equilibrium to avoid deformation of the gas-tight membrane in the cell. The water circulates between the 2 electrodes either side of the membrane. The electrodes are subjected to an electric current, generated by a direct current supply of imposed intensity (10 to 35 A). The resulting voltage depends on the conductivity of the water (temperature, type and quantity of mineral salts: mobility charges), on the distance between the two electrodes and on the type of membrane used. In the tests under consideration, the voltage varies between 8 and 45 V.

By using water $Cl^-$ and $Br^-$ ion-free water, it is ensured that halogen species (in particular chlorine and bromine species) and other electrolysis by-products are not generated. Therefore, with the method of the invention, it is possible to obtain oxygen-enriched water free of undesirable species (but which are conventionally generated by electrolysis of water—potable water, surface water, spring water—not previously treated) in particular bromate ions $BrO_3^-$, chlorate ions $ClO_3^-$, chlorine $Cl_2$, hypochlorite $ClO^-$, hypochlorous acid HC10, ozone $O_3$ and trihalomethanes. Amongst the halogen species, and although much less frequent in water, care is also taken to avoid the presence of iodine ions $I^-$ to prevent any generation of by-products such as iodine $I_2$ or iodates $IO_3^-$.

However, to allow the conducting of electrolysis, this $Cl^-$ and $Br^-$ ion-free water must comprise dissolved salts (it is these dissolved salts which are the charge carriers and therefore enable electrolysis).

The $Cl^-$ and $Br^-$ ion-free water is advantageously water which has undergone a demineralization step intended to remove these $Cl^-$ and $Br^-$ ions, then a remineralization step (addition of pure salts). The elements that are particularly targeted in this demineralization step are the chlorides and bromides from which the chlorine and bromine oxidants are generated during oxidation at the anode. The starting water can be spring water, underground water or surface water including public mains water.

Prior to the demineralization step, the water can be subjected to one or more softening treatments by passing it through ion exchange resins to remove the hardness of the water (calcium and magnesium) and for dechlorination (if necessary) by passing the water through activated carbon.

According to one advantageous variant of the invention, at step (a) the remineralized permeate can be used which is recovered after reverse osmosis (a1) of the water followed by (a2) remineralization. Therefore, the method of the invention advantageously comprises a prior water treatment step (a1) by reverse osmosis so as to collect a permeate free of $Cl^-$ and $Br^-$ ions; then a prior step (a2) subsequent to step (a1) to remineralize the permeate obtained at step (a1), step a) then being conducted on this remineralized permeate.

Reverse osmosis is a liquid phase separation process by permeation through semi-selective membranes, under the effect of a pressure gradient. Flow is continuous and tangential to the membrane. Part of the water to be treated divides at the membrane into two parts of different concentrations:
  one part passes through the membrane (permeate; water free of $Cl^-$ and $Br^-$ ions),
  one part which does not pass through the membrane (retentate) which comprises molecules or particles retained by the membrane, namely practically all the minerals, in particular the $Cl^-$ and $Br^-$ ions.

The reverse osmosis module is to be sized according to rules of the art in relation to the characteristics of the untreated water. Reverse osmosis may be preceded by a pre-treatment (filtrations, sterilization, decontamination) to allow optimal conducting thereof.

The conductivity of the obtained permeate is advantageously less than 10 µS/cm. This demineralized water is therefore extremely pure. The maximum content of chlorides and bromides is respectively 0.2 mg/l and 3 µg/l.

This demineralization phase can also be conducted using an older technique than reverse osmosis. Amongst these techniques, mention may be made of distillation or passing the water through ion exchange resins. Electrodialysis is also a valid technique which can be used to carry out this demineralization.

The remineralization step (of the permeate) allows the conducting of the electrolysis reaction. The purpose is to add food quality mineral salts free of chlorides and bromides.

According to one advantageous variant of the invention, the target conductivity varies from 200 to 1000 µS/cm in relation to the target mineralization of the end product. As examples of salts which can be used, the following salts may be particularly cited: $NaHCO_3$, $Na_2SO_4$, $Na_3PO_4$, $Na_2HPO_4$, $NaH_2PO_4$, $KHCO_3$, $K_3PO_4$, $K_2HPO_4$, $KH_2PO_4$, $K_2SO_4$, $MgSO_4$, $CaSO_4$, $Ca(H_2PO_4)2$, $CaHPO_4$, $Ca_5(PO_4)_3OH$. It is essential not to mix salts comprising bicarbonates with calcium or magnesium salts to avoid the precipitation of calcium or magnesium carbonates in the cathode compartment owing to increased pH. In particular, the food salts $Na_2SO_4$ and $Na_3PO_4$, 12 $H_2O$ are added. If necessary, the pH of the water can be modified through the use of compounds well known to those skilled in the art, in particular through the addition of a strong acid or carbonic gas. In particular the pH of the water can be adjusted to pH 7.

According to another variant of the invention, it is possible to increase the target conductivity to over 1000 μS/cm so as optimize the electrolytic production of oxygen. Should the conductivity of the end beverage be lower than that of the water passing through the electrolysis cell, it is possible to reduce this conductivity by subsequent dilution with demineralized water.

The separation of the two electrodes by a membrane generates three major modifications to the treated water:
 change in pH either side of the membrane (acidification on the anode side, alkalinisation on the cathode side);
 migration of ions through this membrane. The ion composition can therefore be modified on the anode and cathode sides;
 water losses since the cathode side with high pH and comprising $H_2$ is difficult to put in value.

In the method of the invention, it is therefore advantageous to re-add the water derived from the cathode compartment of the electrolysis cell, free of hydrogen, to the oxygenated water obtained at step (b). Therefore, the method of the invention advantageously comprises an additional step (c) to re-inject the water derived from the cathode compartment of the electrolysis cell, and free of hydrogen, to the oxygen-enriched water obtained at step (b). Additional step (c), after the electrolysis step, allows self-neutralization. In the cathode branch, after electrolysis, the formed hydrogen is removed as and when it is produced e.g. by a hollow fibre membrane module held under a partial vacuum and advantageously flushed with nitrogen. At the output of the electrolysis unit, the 2 branches (anode and cathode free of hydrogen) join together to form a mixture with neutral pH enriched with $O_2$ and free of $H_2$. This self-neutralization allows the cancelling-out of water losses and ion losses due to the migration of ions either side of the membrane, the mineral composition of the water obtained is therefore fully controlled. With this additional step (c), it is also possible to equilibrate the pressure either side of the membrane separating the 2 compartments, anode and cathode. This self-balancing of pressures increases the lifetime of the membrane by avoiding deformations due to pressure imbalance on either side.

For a beverage, which is acid by nature (pH<3), the acidity at the anode is not a problem. Nonetheless, self-neutralization imparts great simplicity to the method since use is made of the entirety of the water flow entering the module.

The method of the invention may further comprise an additional step (a3) to degas the water prior to the electrolysis step (a) and optionally subsequent to step (a2). Therefore, the oxygen dissolved in the water of the method will solely be oxygen obtained by electrolysis.

The method may comprise a last step, optionally consisting of completing the formulation of the oxygen-enriched water by adding ingredients thereto which cannot undergo the electrolysis reaction subject to irreversible deterioration. These may be mineral salts including chloride forms or organic compounds optionally in salt form, and conventional beverage ingredients: sugars, sweeteners, flavourings, acids, preserving agents, vitamins, plant extracts, juices, proteins, fibres.

Therefore, the method advantageously comprises a subsequent final formulation step (e) comprising the addition of minerals and other conventional beverage ingredients to the water enriched with oxygen by electrolysis. This water may also be completed with vitamins, mineral or organic salts, proteins, plant extracts, and any other natural or synthetic compound compatible with $O_2$. A beverage is thus produced. During this step (d) it is possible to re-inject the retentate of the reverse osmosis obtained at step (a1) to the oxygen-enriched water obtained at step (b) or (c). This step allows the mineral profile of the initial water to be maintained. This assumes that the osmosis equipment is designed to enable this upgrading of the retentate and that no chemical product (of sequestrating type) is injected into the water, to facilitate filtration by reverse osmosis.

The water or beverage thus obtained is then advantageously packaged. Before packaging, the water or beverage may be subjected to a sterilization step (by ultraviolet—UV—for example). Once the final formulation has been obtained, the formulated, oxygen-enriched water or beverage is advantageously stored under pressure and kept cool (5 to 10° C.) to minimize oxygen losses when bottling the beverage. The presence of oxygen imparts the same characteristics to the end product as a gaseous product. Its bottling advantageously implies the same restrictions: iso-barometric bottling machine and specific packaging: Polyethylene Terephtalate PET bottle with gas barrier properties (e.g. multilayer PET or PET with specific coating), glass or aluminium-can type packaging.

FIGS. 1 and 2 show preferred variants of the method according to the invention. The water to be treated A (mains water, surface water, spring water, mineral water) is subjected to demineralization treatment by reverse osmosis (1). Previously, it may undergo a pre-treatment (0) such as filtering and/or sterilization and/or decontamination. At the output of the reverse osmosis module, the permeate A1, water free of chloride and bromide ions, is collected then remineralized (2) through the addition of salts ($NaHCO_3$, $Na_2SO_4$, $Na_3PO_4$ $Na_2HPO_4$ $NaH_2PO_4$, $KHCO_3$, $K_3PO_4$, $K_2HPO_4$ $KH_2PO_4$, $K_2SO_4$, $MgSO_4$ $CaSO_4$, $Ca(H_2PO_4)2$, $CaHPO_4$, $Ca_5(PO_4)_3OH$). The remineralized water A2, still free of chloride and bromide ions, is transferred (3) to the electrolysis cell. Previously, it may be subjected to a gas removal step (in particular of oxygen). Before entering the electrolysis cell, the water A2 or A'2 is separated into two branches, one branch is directed towards the anode compartment (connected to the+pole of the generator)(3b), whereas the other branch is directed towards the cathode compartment (connected to the—pole of the generator)(3a). The dissolved hydrogen comprised in branch C and derived from the cathode compartment is removed. The anode branch A3 and dehydrogenated cathode C' branch are re-joined (self-neutralization, to give A4). It is possible to make provision at the electrolysis cell for recirculation loops (reinjection of part of the anode branch A3 and dehydrogenated cathode branch C' upstream of the electrolysis cell but after separation into 2 branches). The oxygen-enriched water A4 then undergoes a water formulation step (4) i.e. the addition of the ingredients needed for manufacture of the water or beverage, and in particular ingredients which cannot undergo the electrolysis step. According to one advantageous variant, the retentate B derived from the reverse osmosis step is re-added to the water A4 during this formulation step (4). The water or beverage A5 is then packaged (5) in particular by bottling.

It is noted that the method can be conducted by line production and does not require a storage tank.

All the devices and parts used, in particular the membranes and electrodes, are approved for use in the food sector.

With the method of the invention, it is possible to obtain water that is particularly rich in oxygen (the oxygen $O_2$ dissolved in the water resulting directly from the electrolysis process). The method of the invention can therefore advantageously be characterized in that the water obtained at step (b), (c) and (d) comprises at least 100 mg/l of dissolved oxygen, at a temperature of between 5 and 10° C. and at a pressure of $6.10^5$ Pa. Advantageously, after the self-neutralization step (c), the water obtained comprises 150 mg/l of dissolved $O_2$, at a temperature of between 5 and 10° C. and a pressure of $6.10^5$ Pa.

The method allows oxygen-enriched water to be obtained by line production and not batch production, without any water loss.

Once the final formulation is obtained, the formulated oxygen-enriched water or beverage is advantageously stored under pressure and kept cool (5 to 10° C.) to minimize oxygen losses when bottling the beverage.

The inventors have found that over a period of 3 hours after opening the bottle (or pack) enriched with oxygen, the content of dissolved $O_2$ in the water or beverage remains equal to or higher than 90% of the initial content before opening. This excellent stability is observed both for a water or beverage enriched with oxygen by injection of $O_2$ or by using the method of the invention (electrolysis). This evidences a similarity of behaviour of the oxygen between the two enriching methods (injection or electrolysis).

Under normal consumption of the water or beverages i.e. within 3 hours after opening the bottle, the loss of oxygen to be considered remains less than 10% of the initial value before opening. Complete desorption of the supersaturated oxygen requires several days, 23 days in Example 2.

The water or beverage of the invention, before opening or on opening the bottle or pack, advantageously comprises at least 100 mg/l of dissolved oxygen. Advantageously, the water of the invention, in its market pack, comprises at least 100 mg/l of dissolved $O_2$, even at least 110 mg/l of dissolved $O_2$, at an internal pressure varying from between $1,5.10^5$ and $2,5.10^5$ Pa ($1,8.10^5$ Pa) and at ambient temperature.

The oxidation-reduction potential is not modified in the electrolysis method of the invention, insofar as the two anode and cathode compartments are re-mixed after removal of the hydrogen at the output of the electrolysis cell. This means that the oxidation-reduction potential is not very different between an $O_2$ injection method and the electrolysis method developed by the inventors.

A further subject of the invention is an oxygen-enriched water or beverage which can be obtained using the method of the invention, in which the dissolved oxygen is available and usable by cell mitochondria. The dissolved oxygen which can be obtained using the method of the invention, is able to increase mitochondrial respiration rate even when the oxygen content has reached equilibrium concentration (atmospheric $pO_2$ i.e. 10 mg/l). In particular, when the oxygen concentration is limiting, the water or beverage according to the invention is able to maintain a higher oxygen consumption rate and hence greater energy production in ATP form than observed with another water (normal water or water enriched with oxygen by injection) having one same $O_2$ concentration (even at 10 µmol/1=0.32 mg/l).

In an in vitro study on the availability of oxygenated water in mitochondria (cf. Example 3) the inventors have effectively shown that the muscle mitochondria are capable of using all the oxygen present in the enriched water.

The oxygen-enriched water or beverage obtained with the method of the invention is fully available for the mitochondria. Advantageously, the inventors have ascertained that when the oxygen of the solution becomes the factor limiting functioning of the mitochondria, the mitochondrial respiratory rates measured when only the final acceptor of oxygen is functioning (complex IV), are greater with the water of the invention i.e. the water enriched with oxygen by electrolysis compared with a reference water (normal water or water enriched with oxygen by injection). This result suggests that the oxygen dissolved in this form is better available for mitochondria, enabling the latter to maintain a higher oxygen consumption rate and therefore a higher energy production when the oxygen concentration is limiting.

The oxygen-enriched water or beverage which can be obtained using the method of the invention is also characterized in that it allows the production of energy in ATP form to be increased by the mitochondria under intense exercising conditions or when the $O_2$ supply becomes limiting as in patients suffering from arteritis pathologies.

The oxygen-enriched water or beverage able to be obtained with the method of the invention is further characterized in that it allows the supply of $O_2$ to the tissues and organs to be increased. It also enables the hydrating properties of the water to be increased by increasing its absorption and its passing into the intravascular compartment.

Therefore, a further subject of the invention is an oxygen-enriched water or beverage able to be obtained with the method, characterized in that it permits increased absorption and/or retention of the water by the body and can facilitate/improve hydration and/or prevent dehydration.

In an in vivo study in pigs (cf. Example 4), the inventors have effectively shown that the oxygen-enriched water, when obtained using the method of the invention, allows the arterio-venous $O_2$ difference to be increased.

The arterio-venous $O_2$ difference corresponds to the difference between the $O_2$ concentrations of arterial and venous blood, it represents the quantity of $O_2$ consumed by the tissues; it is directly related to the intensity of oxidative metabolism. If a muscle consumes a large quantity of $O_2$, the arterio-venous difference increases at this muscle.

Additionally, in this study, the inventors have also shown that the water enriched with oxygen using the method of the invention, induces an increase in the tissue oxygen partial pressure measured on the skin. The water enriched with oxygen using the method of the invention therefore induces an increased $O_2$ supply to the skin.

$O_2$ consumption (the volume of $O_2$ consumed in $l.min^{-1} kg^{-1}$) increases with the intensity of physical exercise and varies with the age, sex and physiological condition of the subject. During physical effort, the organs on which demand is placed consume more $O_2$ than when resting. After physical effort, the body continues to consume more $O_2$ than when resting until a state of equilibrium is reached, a mechanism called "$O_2$ debt".

This oxygen-enriched water or beverage according to the invention can therefore aid and/or improve physical performance in man (or animal).

A further subject of the invention is an energizing beverage comprising a water or beverage enriched with oxygen according to the invention.

This beverage, in addition to the water of the invention, may comprise all the ingredients conventionally added to a beverage such as sugar, sweeteners, flavourings, acids, preserving agents. This beverage may also be completed with vitamins mineral salts, organic salts, juices, proteins, plant extracts, fibres or any other natural or synthetic compound compatible with $O_2$.

This beverage or water of the invention may in particular be used as energy input, energy booster and/or aid to recovery and return to fitness level, to improve physical performance, to improve tolerance to effort and/or to lengthen physical effort. This beverage or water is therefore particularly suitable for athletes, occasional or regular sports persons. It may be used for indoor sports (fitness in particular) or for any endurance sport to improve performance level and/or to extend physical effort and/or to improve tolerance to effort and/or to aid recovery.

KEYS TO FIGURES

FIG. 1: schematic illustrating a preferred variant of the method according to the invention.

FIG. 2: schematic illustrating a more complete preferred variant of the method of the invention.

FIG. 3: schematic of the electrolysis cell.

FIG. 4: desorption of oxygen, as a function of time, after opening a bottle comprising water enriched with oxygen using the method of the invention by water electrolysis.

FIG. 5: oxygen desorption, as a function of time, after opening a bottle comprising water enriched with oxygen by injection of pure oxygen.

FIG. 6A: maximum mitochondrial respiration (Volume V in µmol $O_2$/min/g dry weight) in relation to the oxygen concentration (expressed as µM of $O_2$) by activating the entire respiratory chain (n=6).

FIG. 6B: maximum mitochondrial respiration (Volume V in µmol $O_2$/min/g dry weight) in relation to oxygen concentration (expressed as µM of $O_2$) by activating solely complex IV of the mitochondrial respiratory chain (n=6).

FIG. 7: trend in arterio-venous oxygen difference (DavO2) in the three groups: reference, electrolysis, injection.

FIG. 8A: relative variations in plasma volume in the three groups (electrolysis, reference and injection) by studying relative changes in haemoglobin and packed cell volume (percentage).

FIG. 8B: relative variations in plasma volume in the three groups (electrolysis, reference and injection) on the basis of osmolarities (in mmol/$kg^{-1}$).

FIG. 9: in vivo trend in pigs of measurements of transcutaneous oxygen partial pressure (TC PO2) in the three reference groups (reference, electrolysis and injection).

The following examples illustrate the invention and are not limiting.

EXAMPLE 1

Method to Prepare Oxygen-Enriched Water (a1) Demineralization

The demineralization step consists of several unit operations grouped together in one unit.

Cooling drinking water from the public mains using a plate exchanger supplied with iced water Delta temperature about −10° C., overpressure pump Softening station with 2 softeners and 2 salt tanks Filtering station:

one 100 µm pre-filter 3 activated carbon filters for dechlorination and parallel removal of organic matter three 1 µm filters for final filtration 1 multicell pump in 316 L stainless steel at input to osmoser 1 reverse osmosis station:

5 pressure vessels equipped with 4-inch membranes (e.g. the membranes marketed under the trade name BWLE 4040)

The osmoser is equipped with needle valves to adjust the flow rates of discarded effluent and recirculation, with input/output manometers and a conductivimeter on the permeate.

1 sterilisation station (UV-C, 254 nm, UV-C dose of 60 mj/$cm^2$ for a flow rate of 2.5 $m^3$/h).

The demienralized water thus obtained is then directed towards a 3.5 $m^3$ storage tank temperature-adjusted via a circulation loop.

(a2) Remineralization

Different salts, either alone or in a mixture, were tested. The chosen food salts to remineralize this purified water are:

Di Sodium Sulphate or $Na_2SO_4$: European Code E514;

Tri Sodium Phosphate or $Na_3PO_4$, 12 $H_2O$; European Code E339.

After adding the salts, the pH of the remineralized water is 10.6-10.7. Neutralization at pH 7 is made by adding food-grade ortho-phosphoric acid (85% extrapure: European Code E338).

The results of the analyses performed on the water at different stages of the method are given in following Table 1:

Type of bottle: glass

Volume: 500 ml

TABLE 1

Results of analyses performed on the water at different stages of the method.

| Sample | pH | Cond. | Ca * | Mg * | Na * | K * | HCO3 * | BrO3 ** | ClO3 ** | SO4 * | PO4 * | NO3 * | Br ** | Cl * |
|---|---|---|---|---|---|---|---|---|---|---|---|---|---|---|
| Water | 7.64 | 504 | 107 | 3.9 | 14.5 | 2.77 | 244 | 4 | 250 | 37 | 0.8 | 31 | 25 | 28 |
| Permeate [1] | 6.02 | 8 | <0.1 | <0.1 | 0.9 | <0.1 | 4.9 | <1 | <20 | 0 | 0 | 0.8 | x | 0 |
| Permeate + salts | 10.7 | 882 | 1.1 | <0.1 | 209 | <0.1 | 165 [2] | <1 | <20 | 257 | 108 | 0.8 | x | 0 |
| Permeate + salts after neutralstn. | 7.19 | 808 | <0.1 | <0.1 | 209 | <0.1 | 97 [2] | <1 | <20 | 255 | 211 | 0.8 | x | 0 |

[1] permeate of reverse osmosis
Cond. conductivity in µS/cm
* concentration expressed in mg/l
** concentration expressed in µg/l
x non-detectable
[2] analytical artefact (a) Electrolysis
*Equipment
  Buffer tank 3.5 m³
  Centrifugal pump
  Water cooler
  Plate exchanger
  Contactors with hollow fibre membranes
  Electrodialysis module equipped with anode in titanium coated with platinum, cathode in 304 stainless steel, and membrane pervious to electric charges, to cations and impervious to gases, of type CMX-Sb (Neosepta® range, manufacturer Tokuyama)
  Multi-parameter analyzer of dissolved oxygen+probe ($O_2$)
  Multi-parameter analyzer of dissolved gas: $O_2$, $O_3$, $H_2$ specific probes ($O_3$) and ($H_2$)
  UV-C sterilizer 254 nm (nominal flow rate: 0.75 m³/h)
  Iso-barometric bottling system consisting of a pressurisable storage tank, temperature-adjusted via a double jacket, and isobarometric filler
  gas filter 0.2 µm.
*Operating Mode The remineralized water is directed towards the pump which ensures a supply pressure of $6.10^5$ Pa at the input to the electrolysis unit. To limit heating due to the pump, the water is then cooled through a plate heat exchanger countercurrentwise to the cooler circuit, which allows the water temperature to be kept at between 4 and 8° C.

A needle valve is used for fine-tuning of the pressure supplied to the electrodialysis unit at about $6.10^5$ Pa.

The residual dissolved gases are then removed by means of 2 membrane contactors in series, setting up a partial vacuum ($0.045.10^5$ Pa) with a suction pump. A sampling point connected to an analyzer equipped with an oxygen probe is used to measure the residual oxygen. The quantity of residual dissolved oxygen is less than 1 mg/l for a maximum water flow rate of 50 l/h. Over and above this water flow rate, the de-aeration performance of mini-modules does not allow such low values of dissolved oxygen to be reached.

The water circuit then divides into 2 branches to supply the cathode and anode of the electrolysis cell. The input/output water flow rate varies from 10 to 50 l/h for the total of the two branches (anode+cathode). The water pressures at the input to the anode and cathode are controlled; they must be balanced to avoid deformation of the gas-tight membrane in the electrolysis cell.

The water circulates between the 2 electrodes, either side of the membrane. The electrodes are subjected to an electric current, generated by a supply of direct current of imposed intensity (10 to 35 A). In the tests under consideration, the voltage varies between 8 and 45 V.

At the output of the cathode, a contactor with hollow fibre membranes allows removal of the hydrogen produced by the electrolysis reaction. This contactor functions under a partial vacuum of $-0,8.10^5$ Pa and light flushing with nitrogen. It allows the dissolved hydrogen to be reduced by a factor of 10 (from 2.5 mg/l to 0.2 mg/l). The hydrogen collected is evacuated and treated to avoid any risk of explosion.

On each branch, there is a recirculation loop which provides better hydraulics in the electrolysis cell: improved mixing of water and gas (turbulent flow), entraining of the gas boundary layer which may form on the surface on the anode. A gear pump permits this recirculation which is controlled by a flowmeter. The recirculation flow rate is about 120 l/h. This recirculation remains optional. It is more advantageous deliberately to choose conditions of pressure and temperature which allow the formation of gas pockets to be avoided. Recirculation then becomes unnecessary. The water is re-mixed with remineralized water which has not yet been subjected to the electrolysis step on entering the cell. Having regard to the input pressure of the system, the recirculation loops are equipped with check valves. In addition to the hydraulic benefit, the loop also allows higher enrichment with oxygen.

The output flow rate (excluding recirculation) is measured using flow meters and can be adjusted by means of needle valves. The pressure in each branch is also measured by means of needle manometers to assess the loss of pressure in the cell. The pressure in each branch is $6.10^5$ Pa; the pressure loss is less than $1.10^5$ Pa.

The 2 branches, anode and cathode, are then re-mixed which offers four advantages:
  self-neutralization between the $H^+$ and $OH^-$ ions produced at the anode and cathode respectively. The resulting pH is therefore neutral;
  elimination of possible variations in mineral composition related to ion transfers either side of the membrane;
  recovery of the entirety of the water, hence an excellent yield,
  self-balancing of pressures either side of the membrane which eliminates the phenomenon of membrane fatigue and increases its lifetime.

On each side of the membrane, the oxidation-reduction reaction is the following:
  Oxidation at the anode (connected to the+pole of the generator): $2H_2O \rightarrow O_2 + 4H^+ + 4e^-$
  Reduction at the cathode (connected to the–pole of the generator): $4H_2O + 4e^- \rightarrow 2H_2 + 4\ OH^-$
globally corresponding to the reaction $2H_2O \rightarrow 2H_2 + O_2$ Measurements of pH and conductivity on each side of the membrane give the following results:

| | | |
|---|---|---|
| Anode | pH = 2.4 | X = 1300 µS/cm |
| Cathode | pH = 11.6 | X = 1400 µS/cm |

The high conductivity values are due to the presence of $H^+$ or $OH^-$ ions.

This conductivity is reduced after the self-neutralization step.

The measurements on the self-neutralized water are the following:
  pH=7.1-7.2  X=750-770 µS/cm  dissolved $O_2$=140-160 mg/l Said oxygen value ensures that the content of dissolved oxygen in the end container (e.g. bottle) is at least 100 mg/l.

The water is then sterilized by UV and stored in a pressurized tank under sufficient oxygen pressure ($2,2.10^5$ Pa of $O_2$) to limit or prevent any degassing/desorption.

NB: The storage tank is filled under pressure. This storage tank is held at a temperature of 5° C. by passing iced water inside the double jacket.

*Electrolysis cell 2 configurations can be used in this method: planar or cylindrical electrodes. The cell used comprises:
  a system to clamp the stack of different parts forming the electrolysis cell,
  2 machined units, in polypropylene, used to distribute water either side of the membrane,
  1 pair of seals in EVA (Ethyl Vinyl Acetate) placed at the rear of each electrode,
  1 pair of seals in PEX (high density crosslinked polyethylene) placed at the front of each electrode to channel the flow of water in contact with the electrodes, 1 pair of openwork separators, maintaining the space between the electrode and the membrane, 2 electrodes: one (1) anode supplied by the positive pole, one (1) cathode supplied by the negative pole of the direct current generator. Each electrode has a unit surface of about 6 dm$^2$.

1 membrane pervious to cations but impervious to gases, allowing the anode compartment to be separated from the cathode compartment.

A scheme of the electrolysis cell is given in FIG. 3.

The cathode is in grade 304 stainless steel, which brings a reduction in the cost of the method as compared with a cathode in solid titanium and platinum coating. The savings generated is around 20% of the full cost of the installation. This choice allows the mixing of flows such as described above, since the stainless steel electrode is food-safe unlike other electrodes.

The anode is also a food-safe electrode. An anode in titanium is used coated with a thin layer of platinum. Manufacturers include De Nora. Titanium offers excellent conduction properties and platinum forms a protective layer against the oxidation phenomenon. Through its nature, the anode requires certain precautions of use. Current density being one of the limiting factors, it is possible to work at densities of 30 mA/cm$^2$ but unadvisable to exceed 100 mA/cm$^2$ otherwise electrode deterioration will be accelerated.

The membrane used is characterized by its imperviousness to gases, which allows O$_2$ to be confined on the anode side and H$_2$ on the cathode side.

As examples of commercially available membranes which may be used, particular mention may be made of the membranes:

Nafion®: manufactured by DuPont de Nemours, widely used in fuel cell technology. This cationic membrane is a sulphonated tetrafluoroethylene copolymer which, when wet, has very good capability for the transporting of protons (H$^+$) whilst having good mechanical and heat resistance. It has better resistance to oxidation and to certain chemical products (chlorine, sodium hydroxide) than Neosepta® membranes. Its cost on the other hand is much higher than the latter.

Neosepta®: CMX membranes are symmetrical, non-oriented cationic membranes in styrene-divinylbenzene copolymer. They are produced by Tokuyama.

CMX-Sb: dense, standard, cationically non-selective, food-grade membrane, much cheaper than the Nafion® membrane. It is this membrane which was chosen on completion of our tests.

CMX-S: monovalent-cation selective membrane. Food-grade approval in Europe, FDA approval pending.

In general, cleaning conditions are limited by the resistance of the anode and membrane. Applicable preparations are:

0.1 N HCl or HNO$_3$ 0.1 N NaOH at 40° C. maximum

Non-ionic surfactants, of Ultrasil® 130 type by Ecolab active Oxonia®, a mixture of oxygenated water and peracetic acid: 1% at 30/40° C.

Measurements of oxidation-reduction potentials:

Demineralized water and remineralized water: +180 mV (Ag/AgCl electrode) i.e. +390 mV with hydrogen reference electrode Water enriched to 100 mg/l O$_2$ by injection: +180 mV (Ag/AgCl electrode) i.e. +390 mV with hydrogen reference electrode Water enriched to 100 mg/l O$_2$ by electrolysis: +145 mV (Ag/AgCl electrode) i.e. +355 mV with hydrogen reference electrode.

EXAMPLE 2

Measurement of Dissolved Oxygen Stability

The objective of this example is to study the stability of the dissolved oxygen, after opening the bottle. The purpose is therefore to characterize degassing kinetics of the beverage on opening the bottle.

Operating Mode

This operating mode is based on a desire to test products representing industrial conditions used for the production of beverages. Therefore, each series of samples is produced within one same fully homogeneous batch, with identical packaging characteristics: format and geometry of bottles, material, stopper, volume of head space (i.e. the volume of gas lying above the water in a sealed bottle).

a. Definition of the product: The samples solely consist of potable water, whose mineral composition has been adjusted, and of oxygen.

b. Composition: The starting water used to prepare the samples is potable water. This potable water was subjected to the electrolysis method of the invention (cf. Example 1) or was enriched with oxygen by injection of pure O$_2$.

The final composition of the water is given in Table 2 below:

TABLE 2

| Na$^+$ (in mg/l) | SO$_4^{2-}$ (in mg/l) | PO$_4^{3-}$ (in mg/l) | Dissolved O$_2$ (in mg/l) | |
|---|---|---|---|---|
| 200 | 251 | 110 | 100 | Value obtained by electrolysis of water |
| 200 | 251 | 110 | 100 | Value obtained by injection of pure O$_2$ | c. Container: The packagings used are the same as those of an industrial production line (750 ml glass bottle and associated crown cap). These conditions guarantee zero permeability of the packaging throughout the product's lifetime i.e. 9 months.

The glass bottles are cleaned then rinsed with MilliQ water before being dried. These bottles are sealed with 26 mm crown caps. The caps are previously sterilized by Gamma radiation. The bottling of the products and final sealing are performed in a controlled atmosphere.

d. Desorption Kinetics—Principle

Once the samples have been prepared, they are stored for at least 48 h at the temperature at which the test is performed, this time corresponding to temperature stabilization and gas equalization between the liquid phase and the head space. The test temperature was deliberately set at 20° C. to approach real consumption conditions.

Three first bottles are analyzed to determine the dissolved gas content at equilibrium before opening. The bottles are then all opened simultaneously in a stable controlled environment. They then remain open throughout the experiment.

At t=0, then at regular intervals for 23 days, 2 bottles from each series tested are sampled and analyzed. On account of the dissolved O$_2$ measuring method, it is necessary to re-cap each bottle with a new cap before proceeding with its analysis. This recapping phase is performed only a few minutes before analysis of the bottles. Each analysis is destructive and is performed in duplicate. Throughout the entire stabilisation phase of the bottles and the tests, the environmental conditions are standardized (ambient temperature, vibrations).

e) Materials and Methods

Analysis of the dissolved oxygen is made by polarographic measurement with a sampling device using bottle piercing.

The bottle is pierced and placed under nitrogen pressure (4 bars) to push the liquid towards the measurement chamber at a flow rate of 60 ml/min. The vector gas is nitrogen since it is scarcely soluble in water and does not disturb analysis.

The oxygen sensor consists of two electrodes, a cathode in platinum and an anode in silver, the whole in an alkaline electrolyte (KCl) separated from the measuring medium by a gas-permeable membrane.

A constant voltage is applied between the 2 electrodes leading to reduction of the oxygen present in the medium. The current generated by the oxidation-reduction reaction is proportional to the quantity of oxygen present in the medium and hence to oxygen partial pressure.

Results

The tests were conducted on 4 series of bottles obtained following the method of the invention and using the method of injecting pure oxygen. For each method, the 4 series correspond to 4 separate values of dissolved oxygen (40, 70, 100, >100 mg/l).

These results evidence a slow decrease in the content of dissolved oxygen (see FIGS. 4 and 5).

Key to FIG. 4 (samples obtained by water electrolysis) and to FIG. 5 samples obtained by injection of pure oxygen):
■ Series 1≈40 ppm
Δ Series 2≈70 ppm
♦ Series 3≈100 ppm
x Series 4>100 ppm The bold line corresponds to the $O_2$ concentration at normal saturation (10 mg/l).

These figures show very slow desorption of the dissolved oxygen (by electrolysis or by injection) after opening the bottles. Complete re-equilibrium with the atmosphere (10 mg/l) in both cases requires 23 days.

For Series 3 and 4 whose initial content is 100 mg/l, instant losses on opening lie between 5 and 10 mg/l and remain less than 10 mg/l including 3 h after opening. These losses are 20 mg/l after 24 h.

Therefore, for normal beverage consumption i.e. within 30 minutes after opening the bottle, the loss of oxygen to be considered remains well below 10% of the initial value before opening.

Complete desorption of the supersaturated oxygen requires 23 days.

Discussion

Over a period of 3 hours after opening the oxygen-enriched bottle, the content of $O_2$ dissolved in the beverage remains equal to or more than 90% of the initial content before opening.

This excellent stability may appear surprising having regard to physical laws governing gas transfers between a liquid and the overhead atmosphere (Henry's law in particular). Nonetheless, some factors can explain said behaviour of the beverage.

These beverages enriched with $O_2$ can be compared with a carbonated drink whose packaging, through its mechanical resistance, allows a state of equilibrium to be maintained at an oxygen partial pressure greater than atmospheric pressure.

The opening of the bottle generates loss of equilibrium through loss of this internal pressure and return to atmospheric pressure. This loss of equilibrium translates as a gradual loss of dissolved $O_2$.

On the other hand, the desorption of excess dissolved $O_2$ is slowed by:
the limited exchange surface between the liquid and the overhead air in the bottle,
the low mobility of $O_2$ in the liquid towards the free surface,
the setting up of a layer of air enriched with oxygen in the immediate vicinity of the surface of the liquid, locally increasing the oxygen partial pressure.

These experiments evidence the similar behaviour of the oxygen between the two enriching methods (electrolysis and injection).

CONCLUSIONS

These results show that with normal consumption of these beverages, i.e. within 3 hours after opening the bottle, the loss of oxygen to be considered remains less than 10% of the initial value before opening. Complete desorption of the supersaturated oxygen requires 23 days.

EXAMPLE 3

In Vitro Study of the Availability and Use of Oxygenated Water in and by the Mitochondria The purpose of this study was 1) to evidence the fact that the oxygen added to the water by electrolysis ($H_2O$ D) is available and usable by muscle mitochondria; 2) to reduce the oxygen concentrations when measuring mitochondrial respiration to approach the $O_2$ concentrations perceived by mitochondria in vivo.

Two respiration solutions (R) prepared with two different waters were tested:
Solution R-A: Reference water ($O_2$ concentration: 10 mg/l).
Solution R-D: water enriched with $O_2$ by electrolysis, but at a similar concentration to the concentration found in the reference water (atmospheric $pO_2$) i.e. 10 mg/l.

It is not necessary to test water enriched with $O_2$ by injection which, at this concentration of 10 mg/l, does not differ from the reference water.

Protocols

Fibre Respiration

With this technique, it is possible to study the properties of all the mitochondria population in situ. The fibres (between 5 and 10 mg fresh weight) are placed in a thermostat-controlled respiration chamber (+22° C.) containing 3 ml of respiration solution enriched with oxygen, and their oxygen consumption is recorded continuously by a Clark electrode connected to a computer.

Protocol 1:

Effect of the Oxygen-Enriched Solution on the Vmax of Muscle Fibres (10 mg of Fibres):

The fibres are placed in the thermostat-controlled respiration chamber (22° C.) and their oxygen consumption is measured either in the R-A solution or in the R-D solution. After recording for 6 minutes, ADP (2 mM) is added and allows the maximum respiration rate of fibres to be reached (Vmax). The ACR (Acceptor Control Ratio) is calculated by determining the ratio between Vmax and $V_0$. It is a good indicator of the functional status of the mitochondria and defines stimulation of respiration by the acceptor (ADP) and permits evaluation of the coupling between oxidations and phosphorylations in the oxygen-enriched solution.

The fibres are left to consume oxygen in solution R for one hour and then the fibres are recovered to be dried and weighed.

Once the experiment is completed, the kinetics of Vmax can be measured in relation to the concentration of oxygen in the tank so as to evidence a possible "qualitative" effect (increase in the affinity of mitochondria for oxygen) of solution R-D on Vmax at high but also low oxygen concentrations.

Protocol 2:

Effect of the Oxygen-Enriched Solution on Complex IV of the Mitochondrial Respiratory Chain:

Complex IV is the final oxygen acceptor in the mitochondrial respiratory chain. The start of this protocol is the same as for Protocol 1, the change occurring after measurement of Vmax or after injecting ADP, when an inhibitor of complex I is added which will inhibit mitochondrial respiration, then succinate is added which allows measurement of mitochondrial respiration via complex II. The following step is the injection into the chamber of an electron donor directly into complex IV (TMPD-ascorbate substrates) to stimulate mitochondrial respiration from cytochrome oxidase (complex IV, terminal oxygen acceptor).

The results corresponding to maximum mitochondrial respiration (Volume V in $\mu$mol $O_2$/min/g dry weight) in relation to oxygen concentration (expressed as $\mu$M of $O_2$) by activating the whole respiratory chain (n=6)-A- or by activating only complex IV of the mitochondrial respiratory chain (n=6)-B— are respectively given in FIGS. 6A and 6B (values± SEM *p<0.05 vs. solution R-A, **p<0.01 vs. solution R-A). The results measured with solution R-A are shown in white, and the results measured with solution R-D are shown in black.

FIGS. 6A and 6B clearly show that the muscle mitochondria are capable of using all the oxygen present in solution R-D, which meets our first objective.

FIG. 6A shows no significant difference between the 2 solutions. This illustrates that when the entire respiratory chain is caused to function, the kinetics of mitochondrial respiration are not significantly different between the two solutions.

Figure 1:
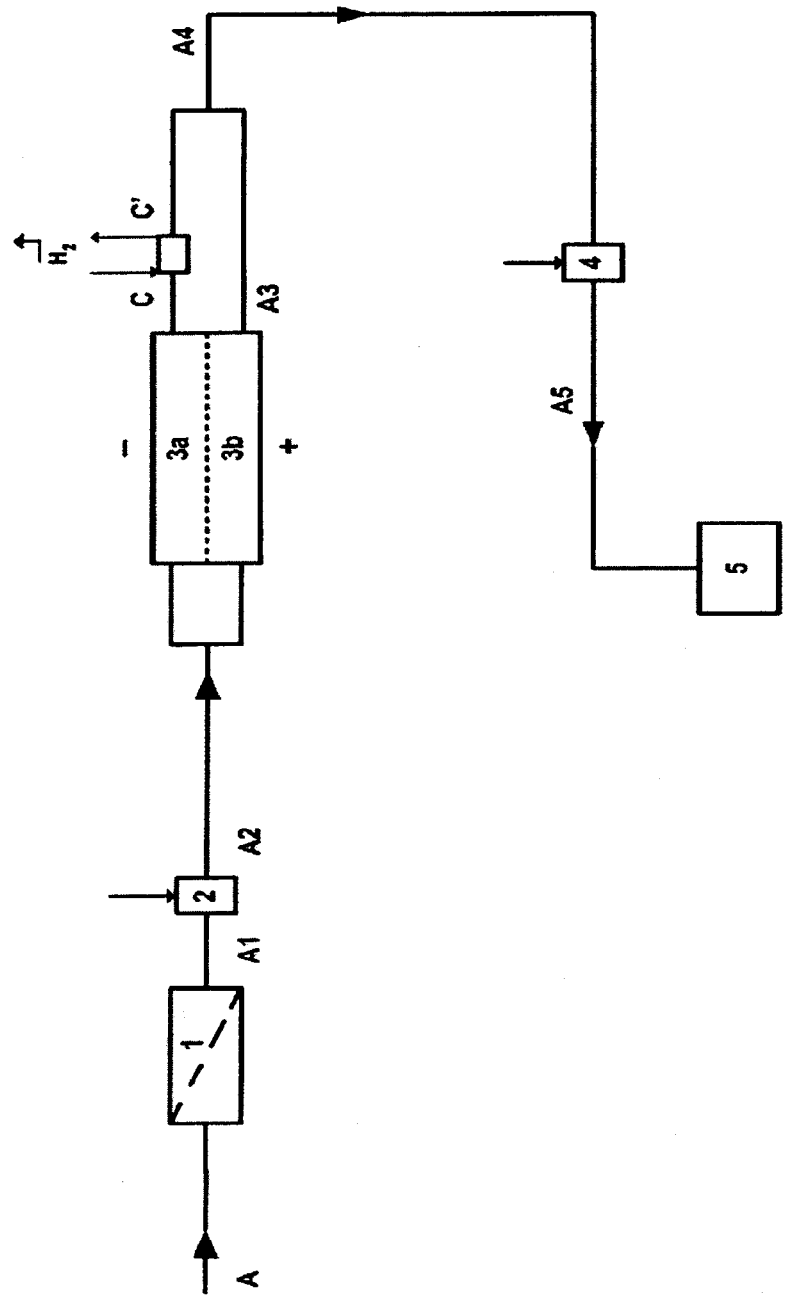
Figure 2:
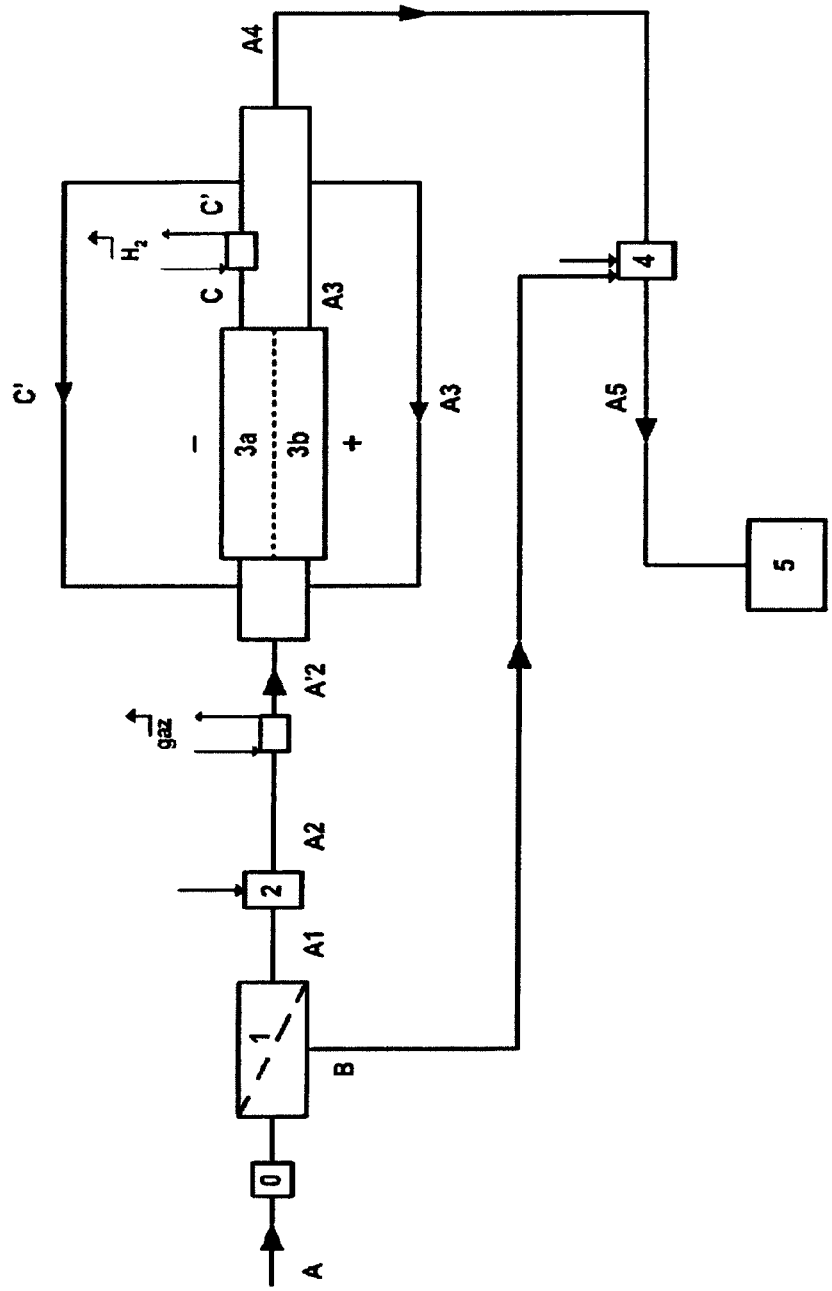
Figure 3:
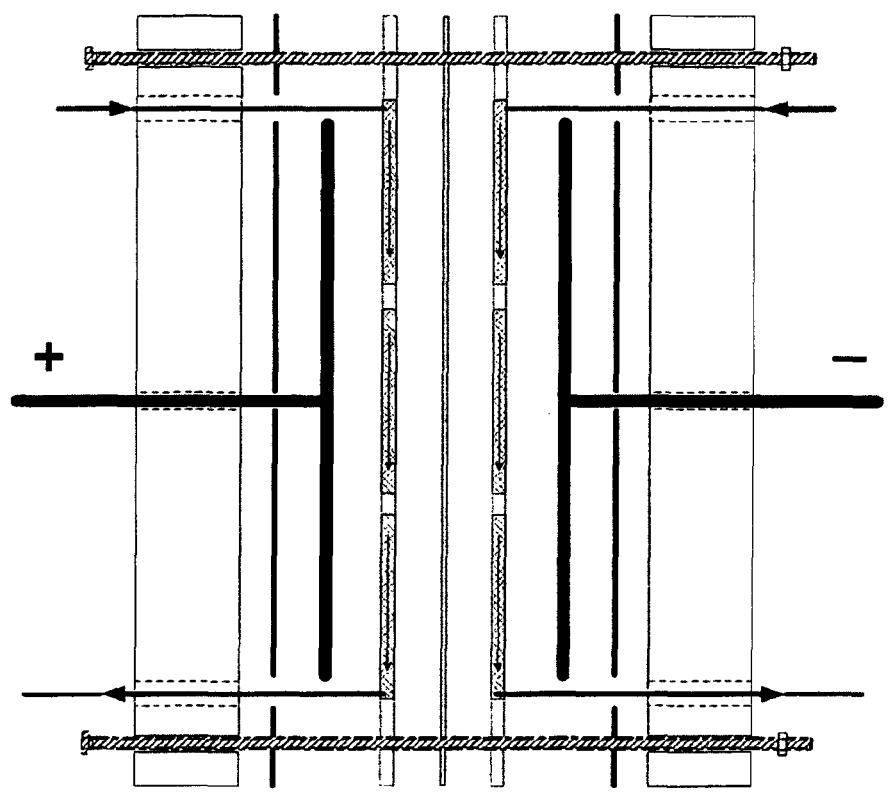
Figure 4:
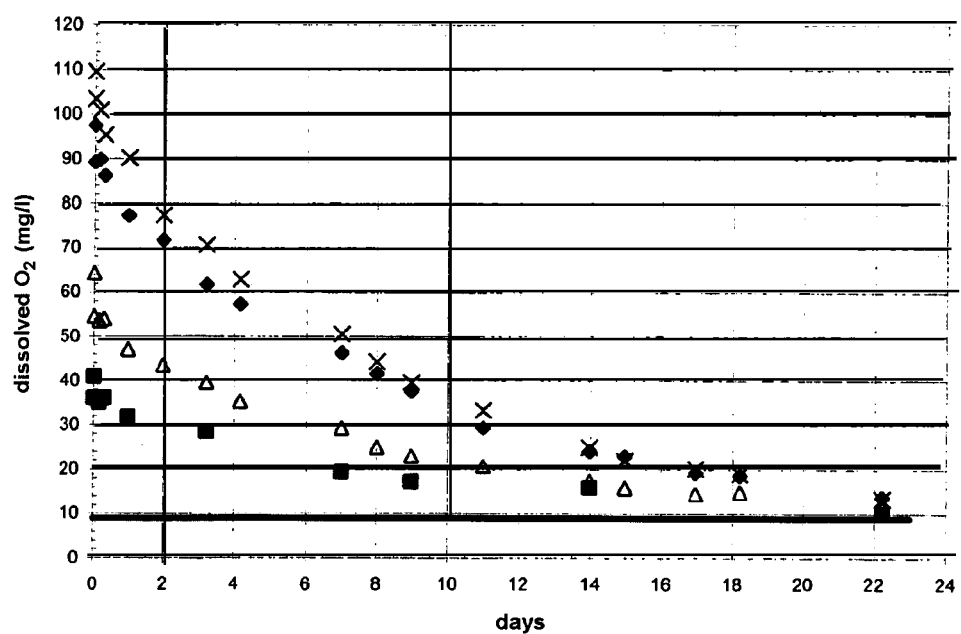
Figure 5:
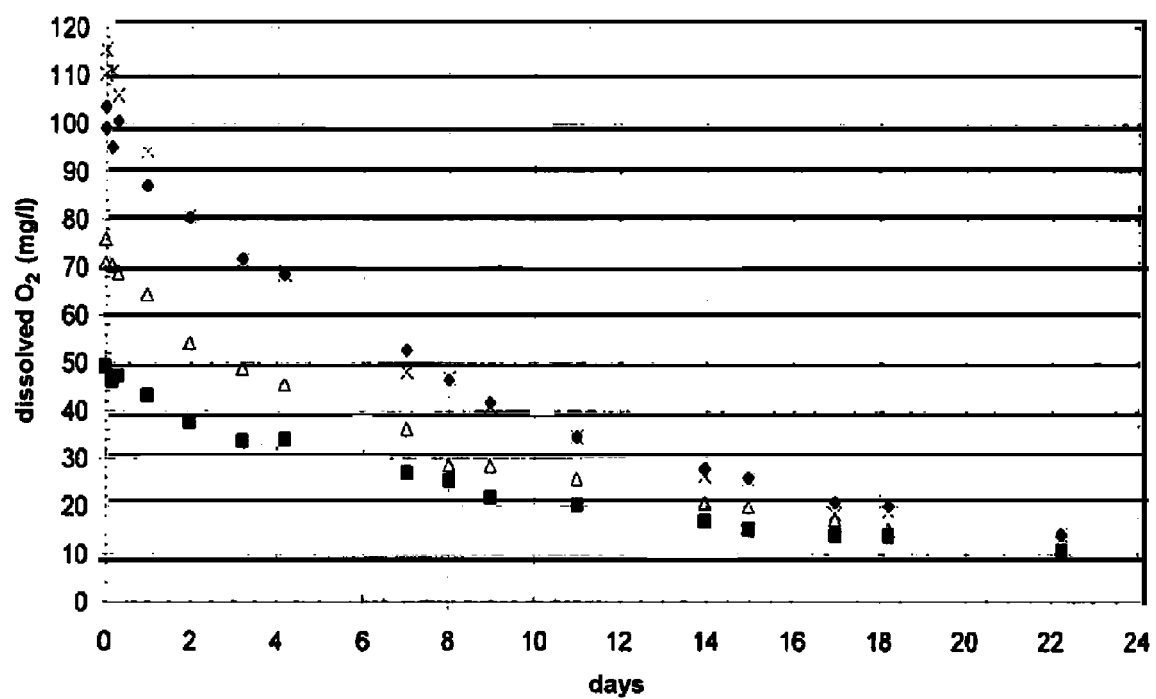
Figure 6:
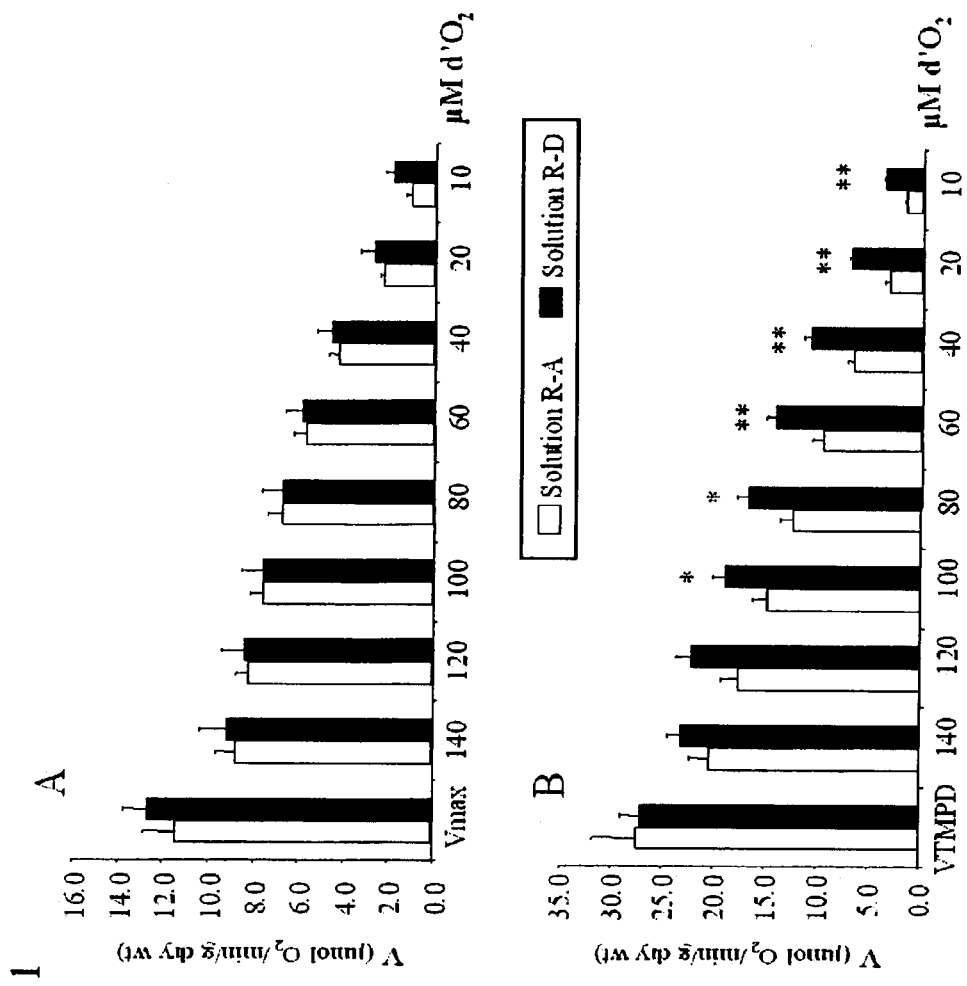
FIGS. 6A and 6B show the mitochondrial respiration rates in relation to the decrease in oxygen concentration in the respiration chamber. $V_{max}$ corresponds to the maximum mitochondrial respiration stimulated by the addition of ADP for the highest $O_2$ concentration.

Most interestingly, FIG. 6B shows that when complex IV is isolated (terminal oxygen acceptor) from the respiratory chain, and when the oxygen concentration becomes limiting (on and after 140 $\mu$M oxygen) the mitochondrial respiration rate becomes higher with the R-D solution by comparison with the R-A solution, this difference becoming significant on and after an oxygen concentration equal to 100 $\mu$M $O_2$ in the respiration chamber (the R-D solution allows an increase of +27% at 100 $\mu$M $O_2$ and up to +65% at 40 $\mu$M $O_2$ by comparison with solution R-A).

To conclude, the water enriched with oxygen obtained using the method of the invention is fully available for the mitochondria. Interestingly, when the oxygen in the solution becomes the factor limiting functioning of the mitochondria, the mitochondrial respiration rates measured when only the terminal oxygen acceptor is functioning (complex IV) are greater with the water of the invention i.e. the water enriched with oxygen by electrolysis compared with the reference water. This result suggests that the oxygen dissolved in this form is better available for the mitochondria, enabling them to maintain a greater oxygen consumption rate and hence an energy production in ATP form that is greater when the oxygen concentration of the medium is limiting.

EXAMPLE 4

In Vivo Study on Pigs

The study was conducted on pigs of small size (Large White): 8 in the oxygen group by electrolysis (Elect), 6 in the reference group without added oxygen (Ref) and 6 in the oxygen group by injection (Inj).

The Elect group consumed water which underwent the electrolysis method according to the invention (cf. Example 1). The Inj group consumed water enriched with oxygen by injection of pure $O_2$.

The final composition of the three types of water is given in following Table 3:

TABLE 3

| Group | Na$^+$ (in mg/l) | SO$_4^{2-}$ (in mg/l) | PO$_4^{3-}$ (in mg/l) | Dissolved $O_2$ (in mg/l) | |
|---|---|---|---|---|---|
| Ref | 200 | 251 | 110 | 10 | Value of $O_2$ in liquid in equilibrium with the atmosphere |
| Elect | 200 | 251 | 110 | 100 | Value obtained by electrolysis of water |
| Inj | 200 | 251 | 110 | 100 | Value obtained by injection of pure $O_2$ |

A volume of water of 10 ml·kg$^-$ was administered. After T0 at the end of intra-gastric administration, samples were taken at: 2½, 5, 10, 15, 20, 25, 30, 35, 40, 50, 60, 75, 90, 105 and 120$^{th}$ minutes. Two-dimensional variance analysis with repeated measurements and Tukey post-hoc analysis were performed on the measurements taken at the 5$^{th}$, 10$^{th}$, 15$^{th}$, 30$^{th}$, 60$^{th}$ and 90$^{th}$ minute after intra-gastric administration.

Trend in Arterio-Venous Differences

Figure 7:
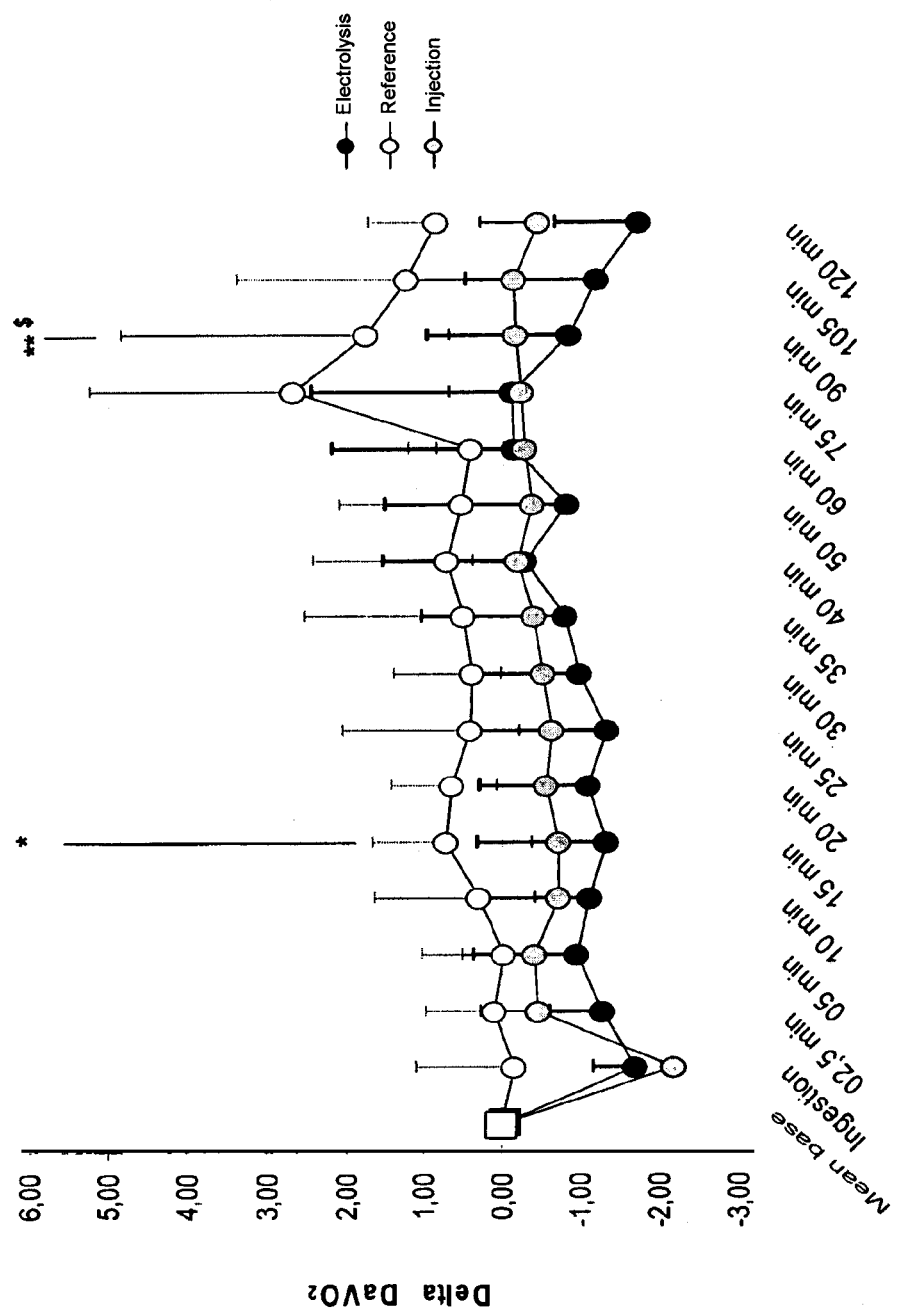

The arterio-venous differences expressed in relative values are significantly lower at the 15$^{th}$ minute in the Electrolysis group compared with the Reference group (FIG. 7, Table 4), this trend being observed with the measurements taken at the 10$^{th}$ and 30$^{th}$ minutes. A significant difference is also observed at the 90$^{th}$ minute between the $O_2$-enriched waters and the reference (FIG. 7, Table 4).

TABLE 4

Trend in arterio-venous oxygen difference (DavO2) in the three groups, relative values and statistical analysis

| | Relative values of DavO2 ml $O_2$ · 100 ml$^{-1}$ (mean ± SD) | | | Simple "group" effects | Tukey test "groups" Significance | | |
|---|---|---|---|---|---|---|---|
| | Electrolysis | Reference | Injection | Value of p | E vs. R | E vs. I | R vs. I |
| 5 min | −0.94 ± 1.32 | −0.03 ± 1.05 | −0.41 ± 0.93 | 0.350 | NS | NS | NS |
| 10 min | −1.12 ± 1.37 | 0.31 ± 1.33 | −0.72 ± 0.32 | 0.071 | NS | NS | NS |
| 15 min | −1.32 ± .1.65 | 0.73 ± 0.94* | −0.71 ± 0.35 | 0.05 | p = 0.05 | NS | NS |
| 30 min | −0.98 ± 1.48 | 0.41 ± 1.00 | −0.51 ± 0.55 | 0.085 | NS | NS | NS |

TABLE 4-continued

Trend in arterio-venous oxygen difference (DavO2) in the
three groups, relative values and statistical analysis

| | Relative values of DavO2 ml $O_2 \cdot 100$ ml$^{-1}$ (mean ± SD) | | | Simple "group" effects | Tukey test "groups" Significance | | |
|---|---|---|---|---|---|---|---|
| | Electrolysis | Reference | Injection | Value of p | E vs. R | E vs. I | R vs. I |
| 60 min | −0.13 ± 2.33 | 0.44 ± 0.77 | −0.26 ± 1.14 | 0.504 | NS | NS | NS |
| 90 min | −0.83 ± 1.81 | 1.75 ± 3.10**$ | −0.17 ± 0.87 | >0.001 | p = 0.01 | NS | p = 0.05 |

E vs. R = Electrolysis versus Reference
E vs. I = Electrolysis versus Injection
R vs. I = Reference versus Injection
*significant difference p < 0.05 between the Reference and Electrolysis groups.
**significant difference p < 0.01 between the Reference and Electrolysis groups.
$significant difference p < 0.05 between the Reference and Injection groups.

Key to FIG. 7: Trend in arterio-venous oxygen difference (DavO2) in the three groups. Results are given in relative values compared with reference basis. A significant difference is found at the 15$^{th}$ (p<0.05) and 90$^{th}$ (p<0.01) minute between the Electrolysis and Reference groups, and at the 90$^{th}$ minute (p<0.05) between the Injection and Reference groups.

Variation in Plasma Compartment

Figure 8A:
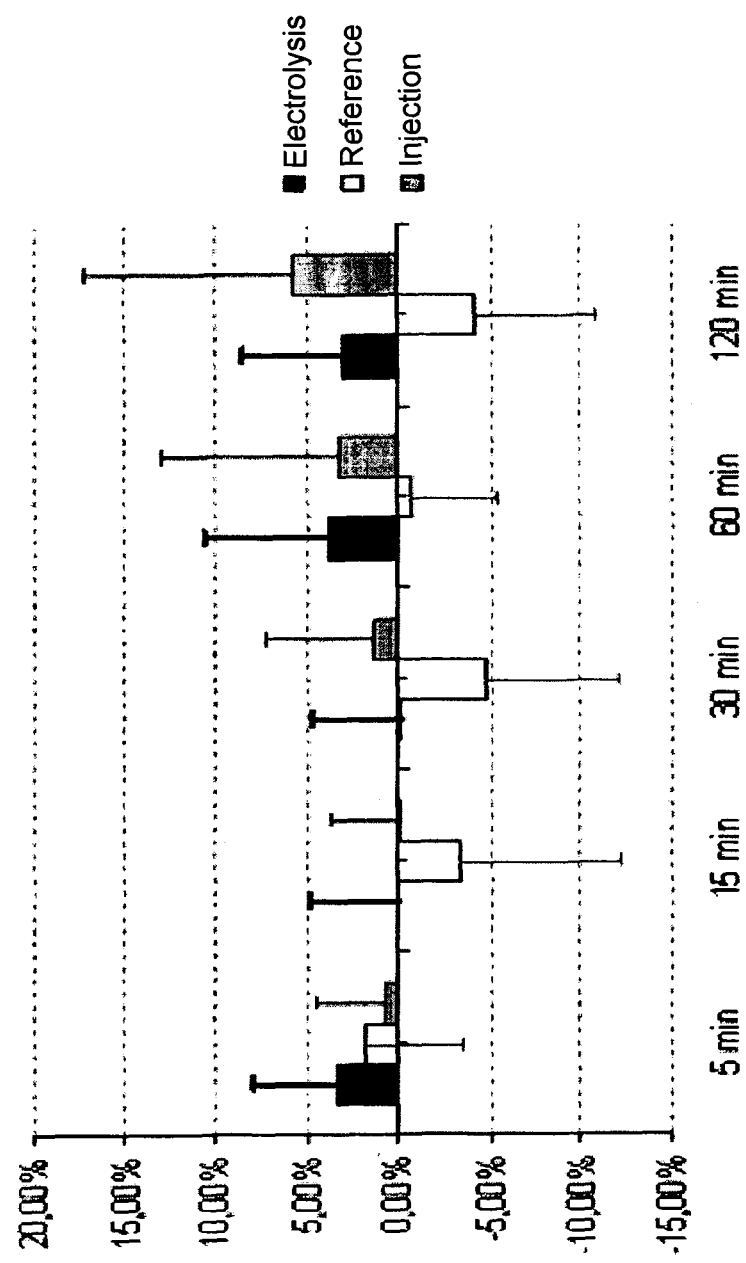
Figure 8B:
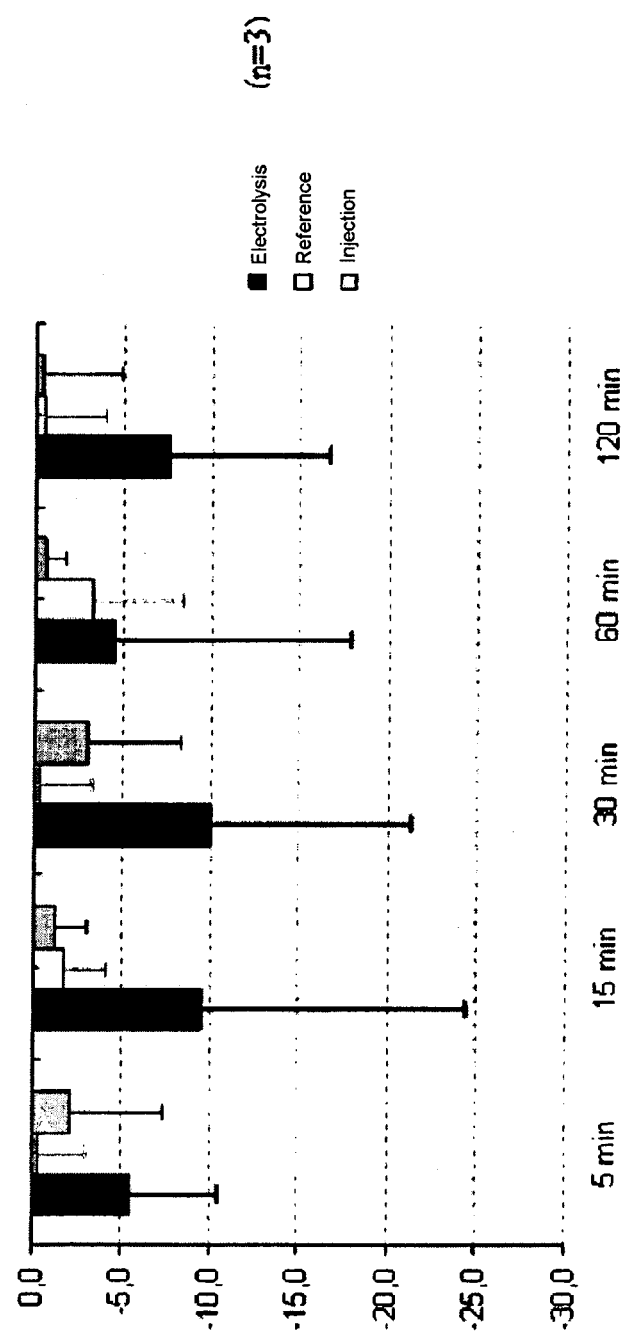

Volume variations in the plasma compartment were determined from relative variations in haemoglobin level and packed cell volume and by measuring osmolarities. Fluctuations are expressed relative to administration time zero (FIGS. 8A and 8B). There is a significant difference between the electrolysis method and the two other experimental situations after 15 and 30 minutes regarding relative variations in osmolarity (Table 5).

TABLE 5

Relative variations in plasma osmolarity
(mmol · kg$^{-1}$) in the 3 groups.

| | Electrolysis | Reference (n = 3) | Injection |
|---|---|---|---|
| 5 min | −5.5 ± 4.9 | −0.2 ± 2.9 | −2.2 ± 5.1 |
| 15 min | −9.5 ± 14.8 | −1.8 ± 2.4* | −1.4 ± 1.7* |
| 30 min | −10.0 ± 11.3 | −0.2 ± 3.0* | −3.0 ± 5.3 |
| 60 min | −4.5 ± 13.4 | −3.3 ± 5.0 | −0.7 ± 1.2 |
| 120 min | −7.5 ± 9.2 | −0.5 ± 3.5 | −0.3 ± 4.5* |

*significant difference p < 0.05 relative to the electrolysis group

Key to FIGS. 8A and 8B: Relative variations in plasma volume in the three groups (electrolysis [black], reference [white] and injection [grey]). These variations are determined firstly by studying relative changes in haemoglobin level and packed cell volume (FIG. 8A, percentage) and secondly from osmolarities (FIG. 8B, in mmol.kg$^{-1}$) calculated on blood samples taken at the 5$^{th}$, 15$^{th}$, 30$^{th}$, 60$^{th}$ and 120$^{th}$ minute. A significant change (*p<0.05) is observed for osmolarity between the Electrolysis group (n=3) and the two other groups at the 15$^{th}$ and 30$^{th}$ minute.

CONCLUSIONS

After intra-gastric administration of $O_2$-enriched water and with respect to arterio-venous oxygen difference (DavO2), a significant difference is observed between the electrolysis method and the reference (Table 4, FIG. 7). Analysis of the three types of water shows that the water enriched with $O_2$ by injection lies between the reference and the electrolysis. However, in the first 90 minutes after ingestion, this water enriched with $O_2$ by injection shows no significant difference in DavO2 compared with the reference group.

Very rapidly after ingestion, for both $O_2$-enriched groups, haemodilution is observed. This observation is confirmed with respect to several independent parameters: variations in haemoglobin level and packed cell volume used to calculate relative variations in plasma volume and changes in plasma osmolarity (FIGS. 8A and 8B). It appears that this effect is promoted by the $O_2$ in the water irrespective of the oxygenation method (electrolysis, injection). Quantitatively however, this effect appears to be higher with the $O_2$-enriched water obtained by electrolysis compared with the $O_2$-enriched water obtained by injection.

EXAMPLE 5

In Vivo Study on Pigs on Transcutaneous Oxygen Partial Pressure (TCPO2)

Material and Methods

The studies were conducted in small-size pigs (Large White). Three groups were formed: a group named "Electrolysis group" consisting of 14 pigs which consumed water enriched with oxygen using the electrolysis method of the invention (cf. Example 1), an "Injection group" consisting of 14 pigs which consumed water enriched with oxygen using the pure $O_2$ injection method, and a "Reference group" consisting of 14 pigs which consumed water without oxygen.

The skin probe to measure tissue $PO_2$ (TC $PO_2$) (Radiometer Copenhagen monitor, series Tina TCM4) was calibrated twice in ambient air. The electrode heated to 45° C. was then placed at the quadriceps muscle after shaving and degreasing the skin with an alcohol solution.

A volume of water of 10 ml·kg$^{-1}$ was administered. The final composition of the three types of water is given in following Table 6:

TABLE 6

| Group | Na$^+$ (in mg/l) | SO$_4^{2-}$ (in mg/l) | PO$_4^{3-}$ (in mg/l) | Dissolved O$_2$ (in mg/l) | |
|---|---|---|---|---|---|
| Ref | 200 | 251 | 110 | 10 | O$_2$ value in liquid in equilibrium with the atmosphere |
| Elect | 200 | 251 | 110 | 100 | Value obtained by electrolysis of water |
| Inj | 200 | 251 | 110 | 100 | Value obtained by injection of pure O$_2$ |

Every 5 minutes for 20 minutes preceding intra-gastric administration of the products (T0) and at 2½, 5, 10, 15, 20, 25, 30, 35, 40, 50, 60, 75, 90, 105 and 120$^{th}$ minutes after T0 at the end of intra-gastric administration, TCPO$_2$ measurements were taken. The TCPO$_2$ values are then expressed as a variation in mm Hg relative to the reference basis (mean of the 4 values obtained during the 20 minutes preceding T0).

Two-dimensional variance analysis on repeat measurements and a Tukey post-hoc test were performed on the measurements taken at the: 5$^{th}$, 10$^{th}$, 15$^{th}$, 30$^{th}$, 60$^{th}$ and 90$^{th}$ minute after intra-gastric administration.

Results

Since metabolic escape in anaesthetized animals occurs after 90 minutes, the values obtained after 90 minutes are not given in the figure.

TABLE 7

Trend in transcutaneous oxygen partial pressure (TC PO$_2$) expressed in mm Hg relative to the base value in the three groups.

| Min | Electrolysis | Reference | Injection | Group effect | p (E/R) | p (E/I) | p (R/I) |
|---|---|---|---|---|---|---|---|
| 5 | 3.90 ± 5.06 | −3.68 ± 3.49 | −1.76 ± 5.83 | 0.005 | 0.05 | NS | NS |
| 10 | 3.33 ± 5.13 | −5.16 ± 3.90 | −2.81 ± 5.76 | 0.001 | 0.05 | NS | NS |
| 15 | 1.97 ± .4.90 | −5.25 ± 4.10 | −1.76 ± 5.83 | 0.01 | 0.05 | NS | NS |
| 30 | 1.69 ± 10.04 | −7.05 ± 7.27 | −3.34 ± 9.11 | 0.005 | 0.05 | NS | NS |
| 60 | −0.44 ± 7.29 | −11.38 ± 5.88 | −6.24 ± 7.85 | 0.001 | 0.01 | NS | NS |
| 90 | −2.74 ± 7.66 | −14.22 ± 7.45 | −9.77 ± 9.50 | 0.001 | 0.01 | 0.05 | NS |

Figure 9:
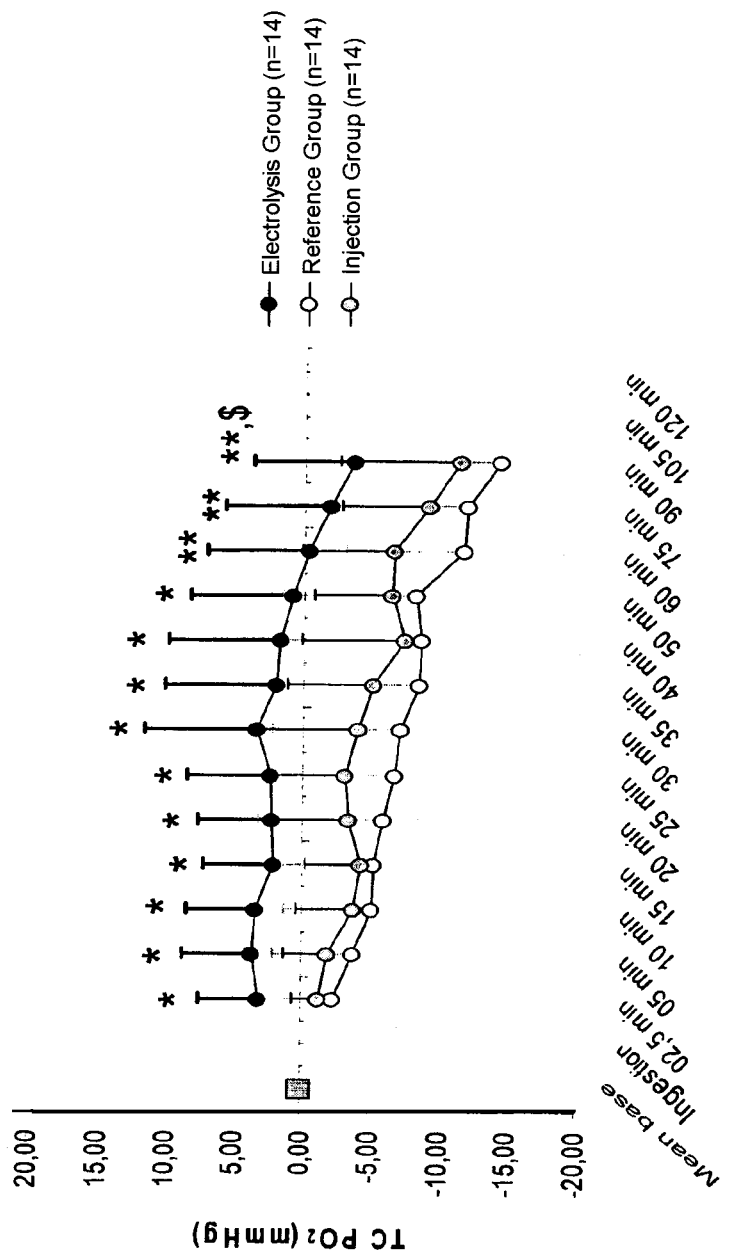

E/R = Electrolysis versus Reference; E/I = Electrolysis versus Injection, R/I = Reference versus Injection
* significant difference p < 0.05 between the Reference and Electrolysis groups
** significant difference p < 0.01 between the Reference and Electrolysis groups
$ significant difference p < 0.05 between the Injection and Electrolysis groups A significant difference is observed between the Electrolysis and the two other groups (Reference and Injection). For example, as early as the 2.5$^{th}$ minute a significant increase in TC PO2 is observed in the Electrolysis group compared with the Reference group (FIG. 9, Table 7). This difference is significant throughout the entire experiment. In addition, at the 90$^{th}$ minute, a significant increase in TC PO2 is observed in the Electrolysis group compared with the Injection group (FIG. 9, Table 7). On the other hand, no difference in TC PO2 is observed between the Injection group and the Reference group (FIG. 9, Table 7).

CONCLUSION

After intra-gastric administration of O$_2$-enriched water, a significant difference is observed between the Electrolysis method and the two other types of water (Reference and Injection) regarding O$_2$ partial pressure measured on the skin (TC PO$_2$). Among the different methods for oxygen enrichment (Electrolysis and Injection) solely oxygen-enrichment by electrolysis allows water to be obtained that is capable of significantly increasing oxygen partial pressure measured on the skin (TC PO$_2$).

The water enriched with oxygen using the electrolysis method of the invention allows the supply of O$_2$ to the skin to be increased.

The invention claimed is:

1. Method to enrich water with oxygen via electrolytic route comprising the following successive steps:
    a) electrolysis of water that is mineralized but free of Cl— and Br— ions, in an electrolysis cell in which the anode and cathode are separated by a membrane pervious to electric charges but impervious to gases, and removal of hydrogen from cathode compartment;
    b) collecting the oxygen-enriched water derived from the anode compartment of the electrolysis cell;
    c) re-injecting the water derived from the cathode compartment of the electrolysis cell, free of hydrogen, into the oxygen-enriched water obtained at step (b); and
    d) packaging the water obtained at step (c) and containing a quantity of dissolved oxygen greater than 50 mg/l.

2. The method according to claim 1, wherein the method further comprises a prior step (a1) to treat the water by reverse osmosis so that the permeate is free of Cl— and Br— ions, then a prior step (a2) subsequent to step (a1) to remineralize the permeate obtained after step (a1) and wherein step a) is conducted on the remineralized permeate.

3. The method according to claim 2, wherein remineralization step (a2) comprises the addition of food salts chosen from the group consisting of NaHCO$_3$, Na$_2$SO$_4$, Na$_3$PO$_4$, Na$_2$HPO$_4$, NaH$_2$PO$_4$, KHCO$_3$, K$_3$PO$_4$, K$_2$HPO$_4$, KH$_2$PO$_4$, K$_2$SO$_4$, MgSO$_4$, CaSO$_4$, Ca(H$_2$PO$_4$)$_2$, CaHPO$_4$, and Ca$_5$(PO$_4$)$_3$OH.

4. The method according to claim 2, wherein the method further comprises an additional step (e) to formulate the water through addition of ingredients compatible with O$_2$ chosen from the group consisting of mineral salts, organic compounds optionally in salt form, sugars, sweeteners, flavourings, acids, preserving agents, vitamins, juices, fibres, proteins, and plant extracts.

5. The method according to claim 2, wherein the method further comprises an additional step (e) to formulate the water through re-injection of the retentate of reverse osmosis obtained at step (a1) into the oxygen-enriched water obtained at step (b) or (c) or (d).

6. The method according to claim 1, wherein the cathode of the electrolysis cell is a cathode in stainless steel.

7. The method according to claim 1, wherein the membrane is a cationic membrane.

8. The method according to claim 1, wherein the method further comprises an additional step (a3) to degas the water prior to the electrolysis step (a) and optionally subsequent to step (a2).

9. The method according to claim 1, wherein the water obtained at step (b), (c), and/or (d) comprises at least 100 mg/l of dissolved oxygen.

* * * * *

UNITED STATES PATENT AND TRADEMARK OFFICE
CERTIFICATE OF CORRECTION

PATENT NO. : 8,709,231 B2
APPLICATION NO. : 12/809461
DATED : April 29, 2014
INVENTOR(S) : Christophe Lascoste et al.

It is certified that error appears in the above-identified patent and that said Letters Patent is hereby corrected as shown below:

In the Claims:

Claim 1, Col. 23, Line 67, "from cathode" should read as --from the cathode--.

Signed and Sealed this
Nineteenth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,709,231 B2                                     Page 1 of 1
APPLICATION NO.   : 12/809461
DATED             : April 29, 2014
INVENTOR(S)       : Lascoste et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 577 days.

Signed and Sealed this

Twenty-ninth Day of September, 2015

Michelle K. Lee
*Director of the United States Patent and Trademark Office*